United States Patent
Zhu et al.

(10) Patent No.: US 9,701,696 B2
(45) Date of Patent: Jul. 11, 2017

(54) METHODS FOR PRODUCING SINGLE CRYSTAL MIXED HALIDE PEROVSKITES

(71) Applicants: Alliance for Sustainable Energy, LLC, Golden, CO (US); Shanghai Jiaotong University, Shanghai (CN)

(72) Inventors: Kai Zhu, Littleton, CO (US); Yixin Zhao, Shanghai (CN)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 15/055,712

(22) Filed: Feb. 29, 2016

(65) Prior Publication Data

US 2016/0251383 A1    Sep. 1, 2016

Related U.S. Application Data

(60) Provisional application No. 62/126,234, filed on Feb. 27, 2015.

(51) Int. Cl.
   C07F 7/00    (2006.01)
   C07F 7/24    (2006.01)
(52) U.S. Cl.
   CPC .................................. C07F 7/24 (2013.01)
(58) Field of Classification Search
   CPC ............................................ C07F 7/24
   USPC ............................................ 556/81
   See application file for complete search history.

(56) References Cited

U.S. PATENT DOCUMENTS

| | | | | |
|---|---|---|---|---|
| 5,871,579 | A | * | 2/1999 | Liang .................. C23C 2/04 117/54 |
| 6,231,666 | B1 | | 5/2001 | Clem et al. |
| 6,429,318 | B1 | * | 8/2002 | Mitzi .............. H01L 21/31691 117/68 |
| 8,563,855 | B2 | | 10/2013 | Pschirer et al. |
| 2004/0191150 | A1 | | 9/2004 | Yano et al. |
| 2010/0301311 | A1 | | 12/2010 | Oku |
| 2011/0300064 | A1 | | 12/2011 | Takeshima |
| 2012/0216865 | A1 | | 8/2012 | Snaith et al. |
| 2014/0020739 | A1 | | 1/2014 | Yang et al. |
| 2014/0060643 | A1 | | 3/2014 | Martin et al. |
| 2014/0332078 | A1 | | 11/2014 | Guo et al. |
| 2015/0129034 | A1 | | 5/2015 | Snaith et al. |
| 2015/0136232 | A1 | | 5/2015 | Snaith et al. |
| 2015/0249170 | A1 | | 9/2015 | Snaith et al. |

FOREIGN PATENT DOCUMENTS

| | | |
|---|---|---|
| CN | 103956394 A | 7/2014 |
| EP | 2 804 232 A1 | 11/2014 |
| WO | WO 2010/085598 A2 | 7/2010 |
| WO | WO 2011/110869 A2 | 9/2011 |
| WO | WO 2011/123117 A1 | 10/2011 |
| WO | WO 2012/162763 A1 | 12/2012 |
| WO | WO 2013/171518 A1 | 11/2013 |
| WO | WO 2014/045021 A1 | 3/2014 |
| WO | WO 2014/097299 A1 | 6/2014 |
| WO | WO 2014/132076 A1 | 9/2014 |
| WO | WO 2014/180789 A1 | 11/2014 |
| WO | WO 2014/181072 A1 | 11/2014 |
| WO | WO 2014/202965 A1 | 12/2014 |
| WO | WO 2015/036905 A1 | 3/2015 |
| WO | WO 2015/166006 A1 | 11/2015 |
| WO | WO 2015/184197 A2 | 12/2015 |

OTHER PUBLICATIONS

"Best Research-Cell Efficiencies", NREL, http://www.nrel.gov/ncpv/images/efficiency_chart.jpg, accessed Apr. 22, 2016, p. 1.

Ball et al., "Low-temperature Processed Meso-superstructured to Thin-film Perovskite Solar Cells", Energy & Environmental Science, 2013, vol. 6, pp. 1739-1743.

Barzykin et al., "Mechanism of Charge Recombination in Dye-Sensitized Nanocrystalline Semiconductors: Random Flight Model", The Journal of Physical Chemistry B, 2002, vol. 106, No. 17, pp. 4356-4363.

Battaglia et al., "Silicon Heterojunction Solar Cell with Passivated Hole Selective $MoO_x$ Contact", Applied Physics Letters, 2014, vol. 104, pp. 113902-1-113902-5.

Bi et al., "Using a Two-step Deposition Technique to Prepare Perovskite ($CH_3NH_3PbI_3$) for Thin Film Solar Cells Based on $ZrO_2$ and $TiO_2$ Mesostructures", Royal Society of Chemistry Advances, 2013, vol. 3, pp. 18762-18766.

Bi et al., "Effect of Different Hole Transport Materials on Recombination in $CH_3NH_3PbI_3$ Perovskite-Sensitized Mesoscopic Solar Cells", The Journal of Physical Chemistry Letters, 2013, vol. 4, No. 9, pp. 1532-1536.

Bisquert et al., "Interpretation of the Time Constants Measured by Kinetic Techniques in Nanostructured Semiconductor Electrodes and Dye-Sensitized Solar Cells", The Journal of Physical Chemistry B, 2004, vol. 108, No. 7, pp. 2313-2322.

Burschka et al., "Sequential Deposition as a Route to High-performance Perovskite-sensitized Solar Cells", Nature, 2013, vol. 499, No. 18, pp. 316-320.

Cai et al., "High Performance Hybrid Solar Cells Sensitized by Organolead Halide Perovskites", Energy & Environmental Science, 2013, vol. 6, No. 5, pp. 1480-1485.

(Continued)

*Primary Examiner* — Sudhakar Katakam
*Assistant Examiner* — Kofi Adzamli
(74) *Attorney, Agent, or Firm* — Michael A. McIntyre (57) ABSTRACT

An aspect of the present invention is a method that includes contacting a metal halide and a first alkylammonium halide in a solvent to form a solution and maintaining the solution at a first temperature, resulting in the formation of at least one alkylammonium halide perovskite crystal, where the metal halide includes a first halogen and a metal, the first alkylammonium halide includes the first halogen, the at least one alkylammonium halide perovskite crystal includes the metal and the first halogen, and the first temperature is above about 21° C.

12 Claims, 5 Drawing Sheets

(56) References Cited

OTHER PUBLICATIONS

Chen et al., "Planar Heterojunction Perovskite Solar Cells via Vapor-Assisted Solution Process", Journal of the American Chemical Society, 2014, vol. 136, No. 2, pp. 622-625.
Chiang et al., "High Voltage and Efficient Bilayer Heterojunction Solar Cells Based on an Organic-inorganic Hybrid Perovskite Absorber with a Low-cost Flexible Substrate", Physical Chemistry Chemical Physics, 2014, vol. 16, pp. 6033-6040.
Choi et al., "Structure of Methylammonium Lead Iodide Within Mesoporous Titanium Dioxide: Active Material in High-Performance Perovskite Solar Cells", Nano Letters, 2014, vol. 14, No. 1, pp. 127-133.
Christians et al., "An Inorganic Hole Conductor for Organo-Lead Halide Perovskite Solar Cells. Improved Hole Conductivity with Copper Iodide", Journal of the American Chemical Society, 2014, vol. 136, No. 2, pp. 758-764.
Chung et al., "All-solid-state Dye-sensitized Solar Cells with High Efficiency", Nature, 2012, vol. 485, pp. 486-489.
Colella et al., "MAPbI3—xClx Mixed Halide Perovskite for Hybrid Solar Cells: The Role of Chloride as Dopant on the Transport and Structural Properties", Chemistry of Materials, 2013, vol. 25, pp. 4613-4618.
Conings et al., "Perovskite-Based Hybrid Solar Cells Exceeding 10% Efficiency with High Reproducibility Using a Thin Film Sandwich Approach", Advanced Materials, Apr. 2014, vol. 26, No. 13, pp. 2041-2046.
Dasgupta et al., "Enhanced Extraction Rates through Gap States of Molybdenum Oxide Anode Buffer", The Journal of Physical Chemistry C, 2013, vol. 117, No. 8, pp. 9206-9211.
Dloczik et al., "Dynamic Response of Dye-Sensitized Nanocrystalline Solar Cells: Characterization by Intensity-Modulated Photocurrent Spectroscopy", The Journal of Physical Chemistry B, 1997, vol. 101, No. 49, pp. 10281-10289.
Docampo et al., "Efficient Organometal Trihalide Perovskite Planarheterojunction Solar Cells on Flexible Polymer Substrates", Nature Communications, 2013, vol. 4, Article No. 2761, pp. 1-6.
Docampo et al., "Solution Deposition—Conversion for Planar Heterojunction Mixed Halide Perovskite Solar Cells", Advanced Energy Materials, 2014, vol. 4, pp. 1-6.
Dualeh et al., "Effect of Annealing Temperature on Film Morphology of Organic-Inorganic Hybrid Perovskite Solid-State Solar Cells", Advanced Functional Materials, 2014, vol. 24, No. 21, pp. 3250-3258.
Dualeh et al., "Impedance Spectroscopic Analysis of Lead Iodide Perovskite-Sensitized Solid-State Solar Cells", ACS Nano, 2014, vol. 8, No. 1, pp. 362-373.
Edri et al., "High Open-Circuit Voltage Solar Cells Based on Organic-Inorganic Lead Bromide Perovskite", The Journal of Physical Chemistry Letters, 2013, vol. 4, No. 6, pp. 897-902.
Edri et al., "Chloride Inclusion and Hole Transport Material Doping to Improve Methyl Ammonium Lead Bromide Perovskite-Based High Open-Circuit Voltage Solar Cells", Journal of Physical Chemistry Letters, 2014, vol. 5, pp. 429-433.
Eperon et al., "Formamidinium Lead Trihalide: A Broadly Tunable Perovskite for Efficient Planar Heterojunction Solar Cells", Energy & Environmental Science, 2014, vol. 7, No. 3, pp. 982-988.
Eperon et al., "Morphological Control for High Performance, Solution-Processed Planar Heterojunction Perovskite Solar Cells", 2014, vol. 24, No. 1, pp. 151-157.
Etgar et al., "Mesoscopic $CH_3NH_3PbI_3/TiO_2$ Heterojunction Solar Cells", Journal of the American Chemical Society, 2012, vol. 134, No. 42, pp. 17396-17399.
Gao et al., "n-Type Transition Metal Oxide as a Hole Extraction Layer in PbS Quantum Dot Solar Cells", Nano Letters, 2011, vol. 11, pp. 3263-3266.
Green et al., "The Emergence of Perovskite Solar Cells", Nature Photonics, 2014, vol. 8, pp. 506-514.
Gretener et al., "Development of $MoO_x$ Thin Films as Back Contact Buffer for CdTe Solar Cells in Substrate Configuration", Thin Solid Films, 2013, vol. 535, pp. 193-197.
Heo et al., "Efficient Inorganic-organic Hybrid Heterojunction Solar Cells Containing Perovskite Compound and Polymeric Hole Conductors", Nature Photonics, 2013, vol. 7, No. 6, pp. 486-491.
Im et al., "6.5% Efficient Perovskite Quantum-Dot-Sensitized Solar Cell", Nanoscale, 2011, vol. 3, pp. 4088-4093.
Jeon et al., "Efficient Inorganic-Organic Hybrid Perovskite Solar Cells Based on Pyrene Arylamine Derivatives as Hole-Transporting Materials", Journal of the American Chemical Society, 2013, vol. 135, No. 51, pp. 19087-19090.
Jang et al., "Voltage-Enhancement Mechanisms of an Organic Dye in High Open-Circuit Voltage Solid-State Dye-Sensitized Solar Cells", ACS Nano, 2011, vol. 5, No. 10, pp. 8267-8274.
Jeon et al., "Solvent Engineering for High-performance Inorganic-organic Hybrid Perovskite Solar Cells", Nature Materials, 2014, vol. 13, No. 9, pp. 897-903.
Jin et al., "Thousandfold Change in Resistivity in Magnetoresistive La—Ca—Mn—O Films", Science, vol. 264, pp. 413-415.
Juarez-Perez et al., "Role of the Selective Contacts in the Performance of Lead Halide Perovskite Solar Cells", The Journal of Physical Chemistry Letters, 2014, vol. 5, No. 4, pp. 680-685.
Kagan et al., "Organic-inorganic Hybrid Materials as Semiconducting Channels in Thin-film Field-effect Transistors", Science, 1999, vol. 286, No. 5441, pp. 945-947.
Kim et al., "Lead Iodide Perovskite Sensitized All-Solid-State Submicron Thin Film Mesoscopic Solar Cell with Efficiency Exceeding 9%", Scientific Reports, Aug. 21, 2012, vol. 2, Article No. 591, pp. 1-7.
Kim et al., "Mechanism of Carrier Accumulation in Perovskite Thin-Absorber Solar Cells", Nature Communications, 2013, vol. 4, Article No. 2242, pp. 1-7.
Kim et al, "High Efficiency Solid-State Sensitized Solar Cell-Based on Submicrometer Rutile $TiO_2$ Nanorod and $CH_3NH_3PbI_3$ Perovskite Sensitizer", Nano Letters, 2013, vol. 13, pp. 2412-2417.
Kim et al., "Organolead Halide Perovskite: New Horizons in Solar Cell Research", The Journal of Physical Chemistry C, 2014, vol. 118, pp. 5615-5625.
Kojima et al., "Organometal Halide Perovskites as Visible-Light Sensitizers for Photovoltaic Cells", Journal of the American Chemical Society, 2009, vol. 131, No. 7, pp. 6050-6051.
Laban et al., "Depleted Hole Conductor-free Lead Halide Iodide Heterojunction Solar Cells", Energy & Environmental Science, 2013, vol. 6, No. 11, pp. 3249-3253.
Lee et al., "Efficient Hybrid Solar Cells Based on Meso-Superstructured Organometal Halide Perovskites", Science, 2012, vol. 338, No. 6107, pp. 643-647.
Liang et al., "Synthesis and Characterization of Organic-Inorganic Perovskite Thin Films Prepared Using a Versatile Two-Step Dipping Technique", Chemistry of Materials, 1998, vol. 10, No. 1, pp. 403-411.
Liang et al., "Additive Enhanced Crystallization of Solution-Processed Perovskite for Highly Efficient Planar-Heterojunction Solar Cells", Advanced Materials, Jun. 2014, vol. 26, No. 22, pp. 3748-3754.
Liu et al., "Efficient Planar Heterojunction Perovskite Solar Cells by Vapour Deposition", Nature, 2013, vol. 501, pp. 395-398.
Liu et al., "Perovskite Solar Cells with a Planar Heterojunction Structure Prepared Using Room-Temperature Solution Processing Techniques", Nature Photonics, 2014, vol. 8, pp. 133-138.
Maeno et al., "Superconductivity in a Layered Perovskite Without Copper", Nature, 1994, vol. 372, pp. 532-534.
Neale et al., "Size and Shape Control of Nanocrystallites in Mesoporous TiO2 Film", Journal of Materials, 2007, vol. 17, pp. 3216-3221.
Nelson et al., "Trap-limited Recombination in Dye-sensitized Nanocrystalline Metal Oxide Electrodes", Physical Review B, 2001, vol. 63, No. 20, pp. 205321-1-205321-9.
Nicolosi et al., "Liquid Exfoliation of Layered Materials", Science, 2013, vol. 340 pp. 1226419-1-1226419-18.
Noh et al., "Chemical Management for Colorful, Efficient, and Stable Inorganic-Organic Hybrid Nanostructured Solar Cells", Nano Letters, 2013, vol. 13, pp. 1764-1769.

(56) References Cited

OTHER PUBLICATIONS

Park, "Organometal Perovskite Light Absorbers Toward a 20% Efficiency Low-Cost Solid-State Mesoscopic Solar Cell", The Journal of Physical Chemistry Letters, 2013, vol. 4, No. 15, pp. 2423-2429.

Park et al., "Enhanced Crystallinity in Organic-Inorganic Lead Halide Perovskites on Mesoporous $TiO_2$ via Disorder-Order Phase Transition", Chemistry of Materials, 2014, vol. 26, No. 15, pp. 4466-4471.

Pellet et al., "Mixed-Organic-Cation Perovskite Photovoltaics for Enhanced Solar-Light Harvesting", Angewandte Chemie, 2014, vol. 53, pp. 3151-3157.

Preda et al., "Films and Crystalline Powder of $PbI_2$ Intercalated with Ammonia and Pyridine", Journal of Materials Science: Materials in Electronics, 2009, vol. 20, Supplement 1, pp. 465-470.

Qin et al., "Inorganic Hole Conductor-Based Lead Halide Perovskite Solar Cells with 12.4% Conversion Efficiency", Nature Communications, 2014, vol. 5, pp. 1-6.

Qiu et al., "All-solid-state Hybrid Solar Cells Based on a new Organometal Halide Perovskite Sensitizer and One-dimensional $TiO_2$ Nanowire Arrays", Nanoscale, 2013, vol. 5, No. 8, pp. 3245-3248.

Saidaminov et al., "High-quality Bulk Hybrid Perovskite Single Crystals within Minutes by Inverse Temperature Crystallization", Nature Communications, Jul. 6, 2015, pp. 1-6.

Schaak et al., "Perovskites by Design: A Toolbox of Solid-State Reactions", Chemistry of Materials, 2002, vol. 14, No. 4, pp. 1455-1471.

Service, "Perovskite Solar Cells Keep on Surging", Science, 2014, vol. 344, p. 458.

Shi et al., "Hole-Conductor-Free Perovskite Organic Lead Iodide Heterojunction Thin-Film Solar Cells: High Efficiency and Junction Property", Applied Physics Letters, 2014, vol. 104, pp. 063901-1-063901-4.

Snaith, "Perovskites: The Emergence of a New Era for Low-Cost, High-Efficiency Solar Cells", The Journal of Physical Chemistry Letters, 2013, vol. 4, No. 21, pp. 3623-3630.

Solbrand et al., "Electron Transport in the Nanostructured $TiO_2$-Electrolyte System Studied with Time-Resolved Photocurrents", The Journal of Physical Chemistry B, 1997, vol. 101, No. 14, pp. 2514-2518.

Stranks et al., "Electron-Hole Diffusion Lengths Exceeding 1 Micrometer in an Organometal Trihalide Perovskite Absorber", Science, 2013, vol. 342, No. 6156, pp. 341-344.

Vasilopoulou et al., "High Performance Organic Light Emitting Diodes Using Substoichiometric Tungsten Oxide as Efficient Hole Injection Layer", vol. 13, 2012, Organic Electronics, pp. 796-806.

Wang et al., "Epitaxial $BiFeO_3$ Multiferroic Thin Film Heterostructures", Science, 2003, vol. 299, pp. 1719-1722.

Wang et al., "Low-Temperature Processed Electron Collection Layers of Graphene/TiO2 Nanocomposites in Thin Film Perovskite Solar Cells", Nano Letters, 2014, vol. 14, pp. 724-730.

Wojciechowski et al., "Sub-150 ° C. Processed Meso-superstructured Perovskite Solar Cells with Enhanced Efficiency", Energy & Environmental Science, 2014, vol. 7, pp. 1142-1147.

Wu et al., "Retarding the Crystallization of PbI2 for Highly Reproducible Planar-Structured Perovskite Solar Cells via Sequential Deposition", Energy & Environmental Science, 2014, vol. 7, pp. 2934-2938.

Xing et al., "Long-Range Balanced Electron- and Hole-Transport Lengths in Organic-Inorganic $CH_3NH_3PbI_3$", Science, 2013, vol. 342, No. 6156, pp. 344-347.

Yella et al., "Nanocrystalline Rutile Electron Extraction Layer Enables Low-Temperature Solution Processed Perovskite Photovoltaics with 13.7% Efficiency", Nano Letters, 2014, vol. 14, pp. 2591-2596.

Yin et al., "Unusual Defect Physics in $CH_3NH_3PbI_3$ Perovskite Solar Cell Absorber", Applied Physics Letters, 2014, vol. 104, pp. 063903-1-063903-4.

Yu-Hallada et al., "Photoexcitation and Photoluminescence Study of Coordination Complexes of Lead Diiodide with Pyridine", The Journal of Physical Chemistry, 1990, vol. 94, No. 19, pp. 7518-7523.

Zhang et al., "A Facile Solvothermal Growth of Single Crystal Mixed Halide Perovskite $CH_3NH_3Pb(Br_{1-x}Cl_x)_3$", Chemical Communications, Mar. 2015, vol. 51, No. 37, pp. 7820-7823.

Zhang et al., "Controllable Sequential Deposition of Planar $CH_3NH_3PbI_3$ Perovskite Films via Adjustable Volume Expansion", NANO Letters, 2015, vol. 15, No. 6, pp. 3959-3963.

Zhao et al., "Charge Transport and Recombination in Perovskite $(CH_3NH_3)PbI3$ Sensitized $TiO_2$ Solar Cells", The Journal of Physical Chemistry Letters, 2013, vol. 4, No. 17, pp. 2880-2884.

Zhao et al., "Effective Hole Extraction Using $MoO_x$.Al Contact in Perovskite $CH_3NH_3PbI_3$ Solar Cells", Applied Physics Letters, 2014, vol. 104, pp. 213906-1-213906-4.

Zhao et al., "Optical Bleaching of Perovskite $(CH_3NH_3)PbI_3$ Through Room-temperature Phase Transformation Induced by Ammonia", Chemical Communications, 2014, vol. 50, No. 13, pp. 1605-1607.

Zhao et al., "$CH_3NH_3Cl$-Assisted One-Step Solution Growth of $CH_3NH_3PbI_3$: Structure, Charge-Carrier Dynamics, and Photovoltaic Properties of Perovskite Solar Cells", The Journal of Physical Chemistry C, 2014, vol. 118, No. 18, pp. 9412-9418.

Zhao et al., "Solid-State Mesostructured Perovskite $CH_3NH3PbI_3$ Solar Cells: Charge Transport, Recombination, and Diffusion Length", The Journal of Physical Chemistry Letters, 2014, vol. 5, No. 3, pp. 490-494.

Zhao et al., "Efficient Planar Perovskite Solar Cells Based on 1.8 eV Band Gap $CH_3NH_3PbI_2Br$ Nanosheets via Thermal Decomposition", The Journal of the American Chemical Society, 2014, vol. 136, No. 35, pp. 12241-12244.

Zhao et al., "Mesoporous Perovskite Solar Cells: Material Composition, Charge-carrier Dynamics, and Device Characteristics", Faraday Discussions, 2014, vol. 176, pp. 301-312.

Zhao et al., "Three-step Sequential Solution Deposition of $PbI_2$-free $CH_3NH_3PbI_3$ Perovskite", Journal of Materials Chemistry A, 2015, vol. 3, No. 17, pp. 9086-9091.

Zhu et al., "Influence of Surface Area on Charge Transport and Recombination in Dye-Sensitized $TiO_2$ Solar Cells", The Journal of Physical Chemistry B, 2006, vol. 110, No. 50, pp. 25174-25180.

International Search Report and Written Opinion for International (PCT) Application No. PCT/US15/33068, mailed Nov. 24, 2015, pp. 1-13.

* cited by examiner

METHODS FOR PRODUCING SINGLE CRYSTAL MIXED HALIDE PEROVSKITES

CROSS-REFERENCE TO RELATED APPLICATIONS

This application claims the benefit of U.S. Provisional Application No. 62/126,234 filed Feb. 27, 2015, the contents of which are incorporated herein by reference in their entirety.

CONTRACTUAL ORIGIN

The United States Government has rights in this disclosure under Contract No. DE-AC36-08GO28308 between the United States Department of Energy and the Alliance for Sustainable Energy, LLC, the Manager and Operator of the National Renewable Energy Laboratory.

BACKGROUND

Solution processed halide perovskites have emerged as a promising material for optoelectronic devices, especially photovoltaics. Strong light absorption, high charge carrier mobility, and a general tolerance to defects has led to much interest in $CH_3NH_3PbX_3$ (X=I, Br, and Cl) perovskites, where the power conversion efficiency has rapidly climbed to above 20% which rivals all other thin film technologies. $CH_3NH_3PbX_3$ (X=I, Br) single crystals have been previously prepared by conventional single crystal growth techniques, which can be complicated for non-specialists. Thus, there is still a need for simpler and more cost-effective methods for single crystal growth of perovskites.

SUMMARY

An aspect of the present invention is a method that includes contacting a metal halide and a first alkylammonium halide in a solvent to form a solution and maintaining the solution at a first temperature, resulting in the formation of at least one alkylammonium halide perovskite crystal, where the metal halide includes a first halogen and a metal, the first alkylammonium halide includes the first halogen, the at least one alkylammonium halide perovskite crystal includes the metal and the first halogen, and the first temperature is above about 21° C. In some embodiments of the present disclosure, the contacting may include a second alkylammonium halide in the solution where the second alkylammonium halide may include a second halogen. The first alkylammonium halide and the second alkylammonium halide may be present in the solution at a ratio defined by $(1-x)/x$, where x is a stoichiometric amount of the second alkylammonium halide, where x may be greater than zero to about 0.5, $(1-x)$ is a stoichiometric amount of the first alkylammonium halide, and the at least one alkylammonium halide perovskite crystal may be at least one alkylammonium dihalide perovskite crystal that may include the metal, the first halogen, and the second halogen.

In some embodiments of the present disclosure, the metal halide may include at least one of $PbBr_2$, $PbI_2$, and/or $PbCl_2$. The first alkylammonium halide may include at least one of $CH_3NH_3Br$, $CH_3NH_3I$, $CH_3NH_3Cl$, $HC(NH_2)_2I$, $HC(NH_2)_2Br$, and/or $HC(NH_2)_2Cl$. The second alkylammonium halide may include at least one of $CH_3NH_3Cl$, $CH_3NH_3Br$, $CH_3NH_3I$, $HC(NH_2)_2I$, $HC(NH_2)_2Br$, and/or $HC(NH_2)_2Cl$, and the second halogen may be different from the first halogen. In some embodiments of the present invention, the solvent may include a polar solvent. The polar solvent may include at least one of dimethysulfoxide, dimethylformamide, γ-butyrolactone, and/or N-methyl-2-pyrrolidone.

In some embodiments of the present invention, the first temperature may be about 40° C. to about 100° C. The maintaining may be for a period of time of greater than 30 seconds to more than 100 hours. In some embodiments of the present invention, the method may include, prior to the maintaining, heating the solution from a starting temperature to the first temperature. The starting temperature may be about 0° C. to about 30° C. The heating from the starting temperature to the first temperature may be achieved in a period of time of about less than 1 minute to about 10 minutes.

In some embodiments of the present invention, the metal halide may be $PbBr_2$, the first alkylammonium halide may be $CH_3NH_3Br$, the second alkylammonium halide may be $CH_3NH_3Cl$, the solvent may be dimethylformamide, the first temperature may be about 50° C., and x may be about 0 to about 0.25. In some embodiments of the present invention, the method may include a molar ratio defined as the sum of the molar amount of $CH_3NH_3Br$ and $CH_3NH_3Cl$ to the molar amount of $PbBr_2$ and the molar ration may be about 0.8 to about 1.2.

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

Figure 1:
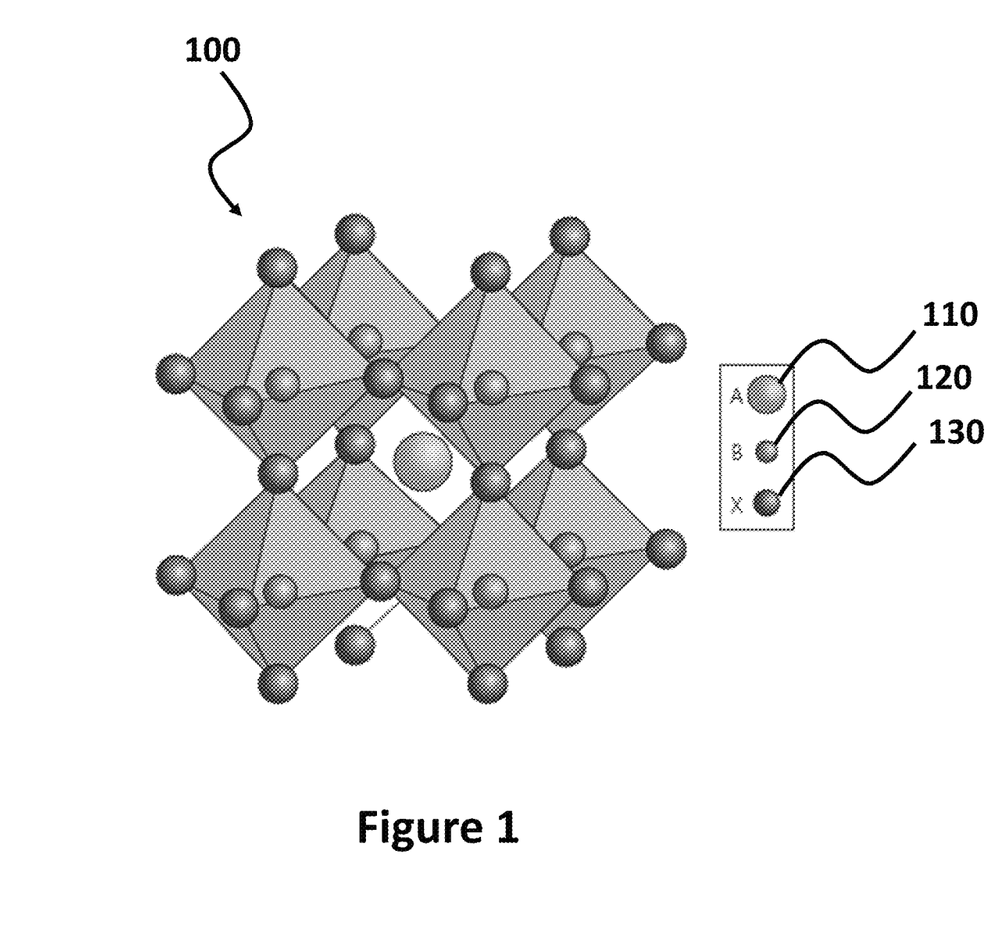
FIG. 1 illustrates alkyl ammonium metal halide perovskite crystal structure, according to exemplary embodiments of the present disclosure.

FIG. 1 illustrates that perovskites halides may organize into cubic crystalline structures, as well as other crystalline structures such as tetragonal and orthorhombic, and may be described by the general formula $ABX_3$, where X (130) is an anion and A (110) and B (120) are cations, typically of different sizes (A typically larger than B). In a cubic unit cell, the B-cation 120 resides at the eight corners of a cube, while the A-cation 110 is located at the center of the cube and is surrounded by 6×-anions 130 (located at the face centers) in an octahedral $[MX_6]^{4-}$ cluster (unit structure). Typical inorganic perovskites include calcium titanium oxide (calcium titanate) minerals such as, for example, $CaTiO_3$ and $SrTiO_3$. In some embodiments of the present invention, the cation A (110) may include a nitrogen-containing organic compound such as an alkyl ammonium compound. Cation (120) may include a metal and anion B (120) may include a halogen.

Additional examples for cation A (110) include organic cations and/or inorganic cations. Organic cations of A (110) may be an alkyl ammonium cation, for example a $C_{1-20}$ alkyl ammonium cation, a $C_1$ alkyl ammonium cation, a $C_{2-6}$ alkyl ammonium cation, a $C_{1-5}$ alkyl ammonium cation, a $C_1$ alkyl ammonium cation, a $C_{1-3}$ alkyl ammonium cation, a $C_{1-2}$ alkyl ammonium cation, and/or a $C_1$ alkyl ammonium cation. Further examples of organic cations of A (110) include methylammonium $(CH_3NH^{3+})$, ethylammonium $(CH_3CH_2NH^{3+})$, propylammonium $(CH_3CH_2CH_2NH^{3+})$, butylammonium $(CH_3CH_2CH_2CH_2NH^{3+})$, formamidinium $(NH_2CH=NH^{2+})$, and/or any other suitable nitrogen-containing organic compound. In other examples, a cation A (110) may include an alkylamine. Thus, a cation A (110) may include an organic component with one or more amine groups. For example, cation A (110) may be an alkyl diamine halide such as formamidinium $(CH(NH_2)_2)$.

Examples of metal cations 120 include, for example, lead, tin, germanium, and or any other 2+ valence state metal that can charge-balance the perovskite halide 100. Examples for the anion X (130) include halogens: e.g. fluorine, chlorine, bromine, iodine and/or astatine. In some cases, the perovskite halide may include more than one anion X (130), for example pairs of halogens; chlorine and iodine, bromine and iodine, and/or any other suitable pairing of halogens. In other cases, the perovskite halide 100 may include two or more halogens of fluorine, chlorine, bromine, iodine, and/or astatine.

Thus, cation A (110), cation B (120), and anion X (130) may be selected within the general formula of $ABX_3$ to produce a wide variety of perovskite halides 100, including, for example, methylammonium lead triiodide $(CH_3NH_3PbI_3)$, and mixed halide perovskites such as $CH_3NH_3PbT_{3-x}Cl_x$ and $CH_3NH_3PbT_{3-x}Br_x$. Thus, a perovskite halide 100 may have more than one halogen element, where the various halogen elements are present in non-integer quantities; e.g. x is not equal to 1, 2, or 3. In addition, perovskite halides, like other organic-inorganic perovskites, can form three-dimensional (3-D), two-dimensional (2-D), one-dimensional (1-D) or zero-dimensional (0-D) networks, possessing the same unit structure.

As stated above, the anion A (110) may include an organic constituent in combination with a nitrogen constituent. In some cases, the organic constituent may be an alkyl group such as straight-chain or branched saturated hydrocarbon group having from 1 to 20 carbon atoms. In some embodiments, an alkyl group may have from 1 to 6 carbon atoms. Examples of alkyl groups include methyl $(C_1)$, ethyl $(C_2)$, npropyl $(C_3)$, isopropyl $(C_3)$, nbutyl $(C_4)$, tertbutyl $(C_4)$, secbutyl $(C_4)$, isobutyl $(C_4)$, npentyl $(C_5)$, 3-pentanyl $(C_5)$, amyl $(C_5)$, neopentyl $(C_5)$, 3-methyl-2-butanyl $(C_5)$, tertiary amyl $(C_5)$, and n-hexyl $(C_6)$. Additional examples of alkyl groups include n-heptyl $(C_7)$, n-octyl $(C_8)$ and the like.

One of the attractive features of lead halide perovskite is the cross substitution of the halides, which can tune the electronic structure (e.g., optical bandgap). An embodiment of the present invention, is a method of preparing for example $CH_3NH_3Pb(Br_{1-8}Cl_8)_3$ perovskite single crystals from dimethylformamide (DMF) precursor solutions containing stoichiometric $PbBr_2$ and $[(1-y) CH_3NH_3Br+ yCH_3NH_3Cl]$. The chemical and physical properties of some of the $CH_3NH_3Pb(Br_{1-8}Cl_8)_3$ perovskites formed by some examples of this method are presented herein and compared to theoretical studies.

Figure 2A:
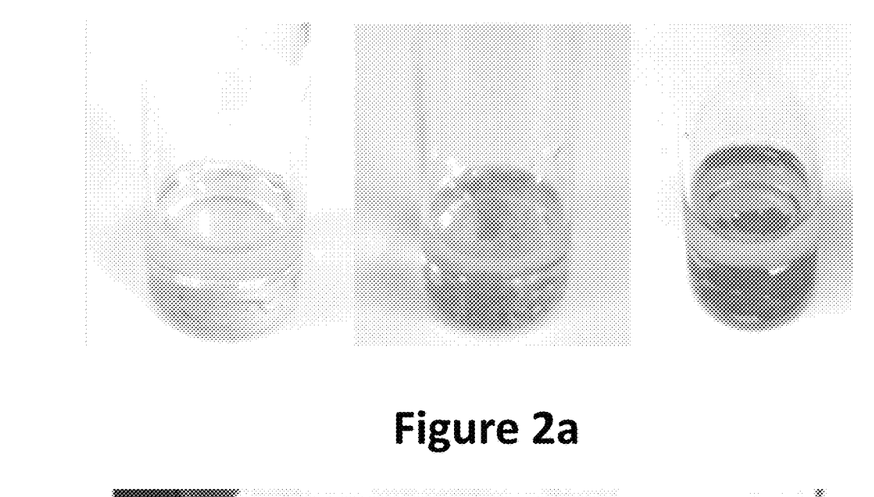
FIG. 2a illustrates the growth of red single crystals in 35 wt % $CH_3NH_3PbBr_3$ DMF solution at 50° C., according to exemplary embodiments of the present disclosure.

In some embodiments of the present disclosure, a $CH_3NH_3PbBr_3$ DMF (or other appropriate solvent) solution may be heated to and/or maintained at a temperature of about 50° C. to form single crystals, for a duration of up to several hours. In some cases, the crystals formed may be characterized by a red color. In some embodiments, heating may be performed without evaporation of the solvent (e.g. DMF). Higher temperatures may be used with a means for condensing the evaporated solvent and refluxing the condensed solvent back to the liquid mixture. Lower temperatures (e.g. cool down to room temperature of about 21° C.) will lead to re-dissolution of the crystals back into the solvent. FIG. 2a shows examples of the growth of some of these red colored single crystals. In this case, small red seed crystals formed first, which subsequently grew into larger crystals with characteristic lengths of up to about 5 mm. It was observed during these experiments that the single crystals formed could be re-dissolved into the solvent (e.g. DMF) after maintaining the single crystals in the precursor solution at room temperature for a period of time; e.g. up to about 12 hours. These observations suggest that crystallization of $CH_3NH_3PbBr_3$ in DMF may be an endothermic reaction and suggests a stronger interaction between $CH_3NH_3Br$ and $PbBr_2$ at higher temperatures than other perovskite reactant mixtures. The crystals illustrated in FIG. 2a, when separated from the solution, were stable in ambient conditions for at least several months without detectable degradation.

Although the method described above utilizes DMF as a solvent for the method to produce single crystal $CH_3NH_3PbBr_3$ perovskites, other polar solvents may be utilized. Thus, some of the solution processing methods described herein may utilize one or more polar solvents including dimethysulfoxide, dimethylformamide, γ-butyrolactone, and/or N-methyl-2-pyrrolidone. Although the method described above heats the perovskite solution to and/or maintains the solution at a temperature of up to about 50° C., higher temperatures may be effective at producing single crystal perovskites. For example, in some examples the solution may be heated to and/or maintained at a temperature up to about 100° C. Higher temperatures may be achieved by performing the crystallization process at pressures above atmospheric pressure. For example, in some examples, the solution crystallization processes described herein may be performed at pressures of about 14.7 psia to about 500 psia (where psia refers to $lb_f/in^2$ absolute). Heating profiles used may be linear, quadratic, and/or any other suitable profile. Other heating profiles may describe step-functions. The starting temperature for such profiles may be room temperature (e.g. about 21° C.) and/or any other ambient, environmental temperature, as defined by the manufacturing environment. The time periods for heating the solution from the starting temperature to the final target temperatures may be from less than about 1 minute to about 10 minutes. The time periods for maintaining the solution at the final target temperature may be from less than 1 hour to more than 100 hours. In some cases, the solvent may be first heated to the desired crystallization temperature (e.g. up to about 50° C.) at which point the remaining reactants may be added (e.g. $CH_3NH_3Br$, $CH_3NH_3Cl$, and/or $PbBr_2$). In some cases, the crystallization may be allowed to proceed at the elevated reaction temperature until a desired average perovskite crystal size is attained.

To understand the factors affecting the crystallization processes of different halides, a theoretical investigation was completed on the crystallization using Vienna Ab-initio Simulation Package (VASP) code with the standard frozen-core projector augmented-wave (PAW) method. This study revealed that the growth of $CH_3NH_3Pb(Br_{1-x}Cl_x)_3$ perovskite from precursor solutions containing stoichiometric $PbBr_2$ and $[(1-y) CH_3NH_3Br+yCH_3NH_3Cl]$ may be energetically favorable, and that it may be energetically unfavorable for the growth of $CH_3NH_3Pb(I_{1-x}Cl_x)_3$ from stoichiometric $PbI_2$ and $[(1-y) CH_3NH_3I+yCH_3NH_3Cl]$ solutions. It appears that the reaction of, $CH_3NH_3Br+CH_3NH_3Cl+PbBr_2 \rightarrow CH_3NH_3Br_2Cl+ CH_3NH_3Br$ may gain an energy of about 0.194 eV, whereas the reaction of, $CH_3NH_3I+CH_3NH_3Cl+PbI_2 \rightarrow CH_3NH_3I_2Cl+ CH_3NH_3I$ may lose an energy of about 0.196 eV.

These results support an experimental observation: $CH_3NH_3Pb(Br_{1-x}Cl_x)_3$ perovskite single crystals may form from precursor solutions containing stoichiometric $PbBr_2$ and $[(1-y) CH_3NH_3Br+yCH_3NH_3Cl]$. The cut-off energy for basis functions was about 400 eV. (Where a "basis set" in theoretical and computational chemistry is a set of functions, called basis functions, which are combined in linear combinations, generally as part of a quantum chemical calculation, to create molecular orbitals. For convenience these functions are typically atomic orbitals centered on atoms, but can theoretically be any function; plane waves are frequently used in materials calculations.) The general gradient approximation (GGA) was used for exchange-correlation. The $\alpha$ phase was considered for the perovskites. For the calculations completed herein, only $x=\frac{1}{3}$ is considered. The calculated energies for various systems are listed below in Table 1.

TABLE 1

| System | Total energy (eV) |
|---|---|
| $MABr + MACl + PbBr_2$ | −95.948 |
| $MAPbBr_3 + MACl$ | −96.101 |
| $MAPbBr_2Cl + MABr$ | −96.142 |
| $MAI + MACl + PbI_2$ | −94.306 |
| $MAPbI_3 + MACl$ | −94.307 |
| $MAPbI_2Cl + MAI$ | −94.110 |

Figure 2B:
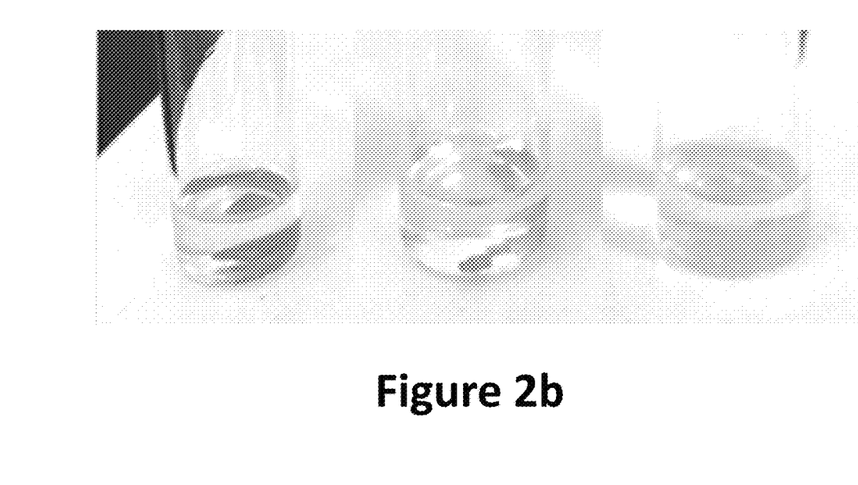
FIG. 2b illustrates the growth of single crystals of $CH_3NH_3Pb(Br_{1-x}Cl_x)_3$, x=0, 0.15, 0.25 from left to right, according to exemplary embodiments of the present disclosure.

Mixed halide perovskite single crystals of $CH_3NH_3Pb(Br_{1-x}Cl_x)_3$ with different Cl/Br ratios were grown using the following precursor solutions: ~0.183 g $PbBr_2$ and ~0.056*(1−y) g $CH_3NH_3Br$ and ~0.034*y g $CH_3NH_3Cl$ was dissolved in 0.443 g DMF to form a $CH_3NH_3PbBr_{3-y}Cl_y$ precursor solution. The solutions were maintained at a temperature of about 50° C. without stirring in a sealed vial until $CH_3NH_3Pb(Br_{1-x}Cl_x)_3$ single crystals formed, which is similar to the growth of $CH_3NH_3PbBr_3$ single crystals. The yellow-to-red mixed halide $CH_3NH_3Pb(Br_{1-x}Cl_x)_3$ single crystals formed in this example, are shown in FIG. 2b. In some embodiments of the present invention, the color of the perovskite crystals may be tuned by adjusting the Cl/Br ratio.

Figure 3:
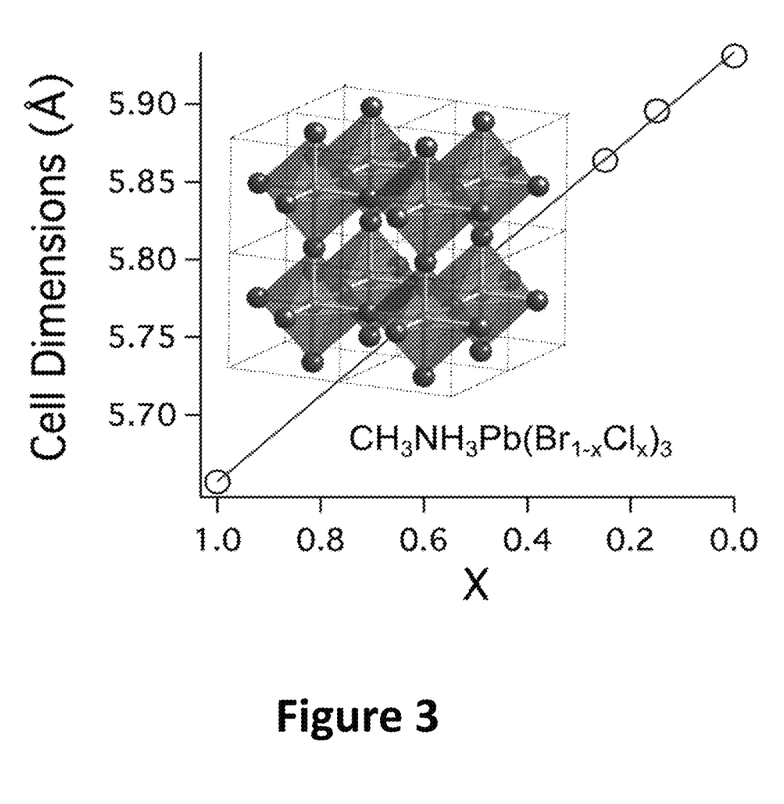
FIG. 3 illustrates the experimentally obtained single crystal XRD cell dimensions for $CH_3NH_3Pb(Br_{1-x}Cl_x)_3$ (x=0, 0.15, 0.25) as a function of chloride inclusion, according to exemplary embodiments of the present disclosure.

FIG. 3 shows the single crystal XRD cell dimensions for $CH_3NH_3Pb(Br_{1-x}Cl_x)_3$ as a function of chloride inclusion, resulting from the experiments described above. The details of the room temperature single crystal diffraction data of the $CH_3NH_3Pb(Br_{1-x}Cl_x)_3$ perovskites produced are summarized below in Table 2.

TABLE 2

| | Compound | | |
|---|---|---|---|
| | $CH_3NH_3PbBr_3$ | $CH_3NH_3Pb(Br_{0.85}Cl_{0.15})_3$ | $CH_3NH_3Pb(Br_{0.75}Cl_{0.25})_3$ |
| empirical formula | $C_2H_6N_1Br_3Pb_1$ | $C_2H_6N_1Cl_{0.45}Br_{2.55}Pb_1$ | $C_2H_6N_1Cl_{0.75}Br_{2.25}Pb_1$ |
| formula weight | 490.99 | 470.98 | 457.63 |
| crystal system | Cubic | Cubic | Cubic |
| lattice parameters | | | |
| a = b = c (Å) | 5.9312(3) | 5.8959(4) | 5.8638(7) |
| α = β = γ (deg) | 90 | 90 | 90 |
| V (Å³) | 208.65(3) | 204.95(4) | 201.62(7) |
| space group | Pm-3m | Pm-3m | Pm-3m |
| Z value | 1 | 1 | 1 |
| Density calc (g/cm3) | 3.554 | 3.664 | 3.395 |
| Wavelength (Å) | 0.71073 | 0.71073 | 0.71073 |
| temperature (K) | 293(2) | 293(2) | 293(2) |
| 2θ max (°) | 54.80 | 55.16 | 54.97 |
| no. obs. [I > 2 sigma (I)] | 74 | 74 | 72 |
| no. parameters | 5 | 5 | 5 |
| goodness of fit on $F^2$ | 1.493 | 1.307 | 1.396 |
| max. shift in cycle | 0.000 | 0.000 | 0.000 |
| residuals: $R_1$; $wR_2$ | 0.0187; 0.0552 | 0.0230; 0.0565 | 0.0396; 0.1019 |
| largest peak | 0.595 | 0.598 | 1.252 |
| deepest hole | −0.809 | −0.703 | −0.943 |

The amount of chloride inclusion was measured by the decrease in cell dimensions in comparison to pure $CH_3NH_3PbBr_3$ and known $CH_3NH_3PbCl_3$ cell parameters. As the ratio of chloride increases, the cell dimensions decreased from about 5.9312(3) Å for the pure bromide, to about 5.8959(4) Å and about 5.8638(7) Å for the 0.15 and 0.25 inclusion of Cl respectively. In all cases the methylammonium cation was disordered on a site of symmetry and the corresponding electron density was removed using the SQUEEZE routine within PLATON (PLATON is a multipurpose crystallographic tool). This suggests that the $CH_3NH_3^+$ cation may freely rotate in the crystal lattice. Theoretical analysis suggests that the energy barrier for $CH_3NH_3^+$ rotation in $CH_3NH_3PbI_3$ may be about 20 meV.

Previous work has shown that $CH_3NH_3Pb(Br_{1-x}Cl_x)_3$ films prepared by spin coating have similar Cl/Br rations to the Cl/Br of their corresponding initial precursor solutions. However, the Cl/Br ratios in the $CH_3NH_3Pb(Br_{1-x}Cl_x)_3$ single crystals produced by the methods described herein were significantly different from their precursor solutions. For example, when the initial Cl/(Br+Cl) ratios in precursor solution of [$PbBr_2$+(1−y) $CH_3NH_3Br$+y$CH_3NH_3Cl$] was 0.08 and 0.17, the Cl/(Cl+Br) ratios of the $CH_3NH_3Pb(Br_{1-x}Cl_x)_3$ single crystals obtained by ICP and single crystal analysis were about 0.15 and 0.25, respectively. This observed change to the molar ratio during the single crystal growth suggests that Cl and Br may have different affinities to form $CH_3NH_3Pb(Br_{1-x}Cl_x)_3$ single crystals, relative to the quick film formation via rapid heating of the spin-coated samples, accompanied with evaporation of solvent (e.g. DMF), using more standard perovskite solution processing methods.

Figure 4A:
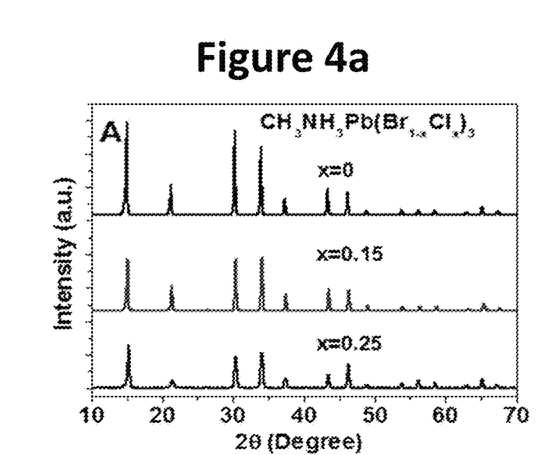
FIG. 4a illustrates the X-ray diffraction (XRD) patterns of $CH_3NH_3Pb(Br_{1-x}Cl_x)_3$ (x=0, 0.15, 0.25) single crystals, produced according to exemplary embodiments of the present disclosure.
Figure 4B:
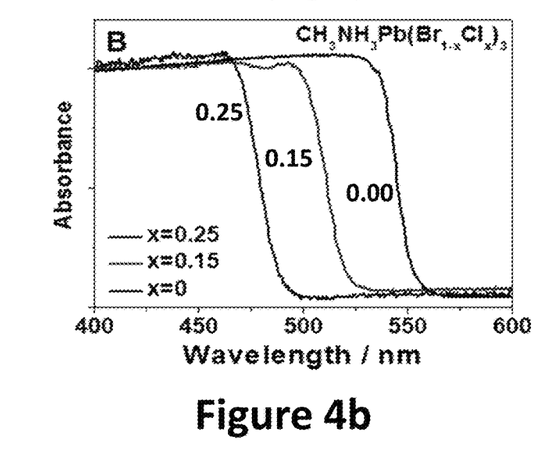
FIG. 4b illustrates the normalized ultraviolet-visible (UV-vis) absorption spectra of $CH_3NH_3Pb(Br_{1-x}Cl_x)_3$ (x=0, 0.15, 0.25) single crystals, produced according to exemplary embodiments of the present disclosure.
Figure 5:
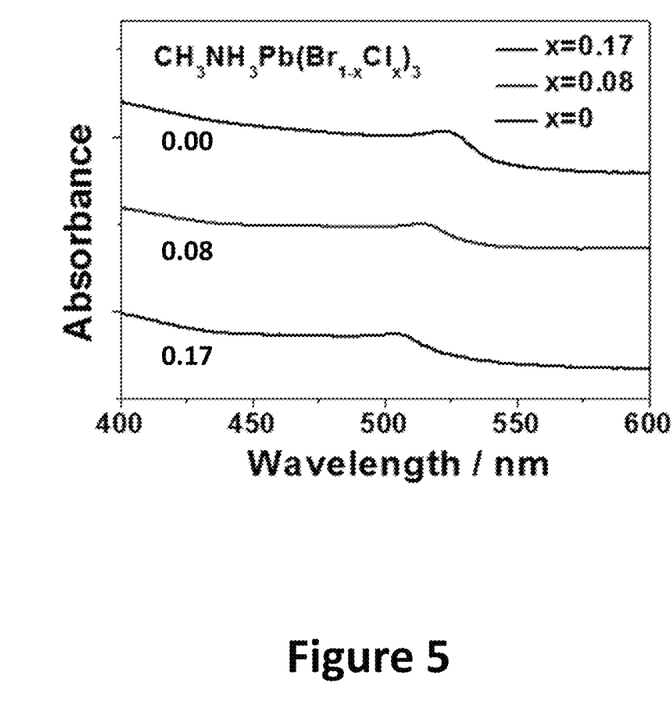
FIG. 5 illustrates the UV-vis spectra of thin films of $CH_3NH_3Pb(Br_{1-x}Cl_x)_3$ perovskites prepared from the precursor solutions of $[PbBr_2+(1-y) CH_3NH_3Br+yCH_3NH_3Cl]$ (y=0, 0.25 and 0.5), corresponding to the Cl/(Cl+Br) ratios of about 0, 0.08, and 0.17, respectively, produced according to exemplary embodiments of the present disclosure.

FIG. 4A shows XRD patterns of ground powders of three exemplary $CH_3NH_3Pb(Br_{1-x}Cl_x)_3$ (x=0, 0.15 and 0.25) single crystals. These patterns show a shifting of characteristic perovskite peaks to higher diffraction angles as a result of increasing the inclusion of Cl. This may suggest that crystal lattices shrink as more Cl is incorporated in the crystals. Reflectance measurements of these single crystals $CH_3NH_3Pb(Br_{1-x}Cl_x)_3$ (x=0, 0.15, 0.25), in powder form, exhibited a blue shift in UV-vis absorbance with increased Cl inclusion as illustrated in FIG. 4B. This may demonstrate that the inclusion of Cl into the perovskite crystals may broaden the bandgap of the crystals. The bandgap of the $CH_3NH_3Pb(Br_{0.75}Cl_{0.25})_3$ is about 2.6 eV, which is about 0.3 eV higher than that of $CH_3NH_3PbBr_3$ (~2.3 eV). The UV-vis spectra of thin films of $CH_3NH_3Pb(Br_{1-x}Cl_x)_3$ perovskites prepared from the same precursor solutions of [$PbBr_2$+(1−y) $CH_3NH_3Br$+y$CH_3NH_3Cl$] (y=0, 0.25 and 0.5) by spin coating are shown in FIG. 5. The bandgap shift was only about 0.1 eV, which is significantly smaller than that for single crystals grown from the same precursor solutions. This observation is consistent with the different Cl/Br ratios observed between the single crystals and spin-coat films from the same precursor solutions.

In some embodiments of the present disclosure, growth of $CH_3NH_3Pb(Br_{1-x}Cl_x)_3$ single crystals using the precursor solution of mixed $PbBr_2$ and (1−y)$CH_3NH_3Br$ with y$CH_3NH_3Cl$, may be grown where y may be less than or equal to 0.5. The presence of $CH_3NH_3I$ may undermine the growth of perovskite single crystal with this method. The formation of $CH_3NH_3Pb(Br_{1-x}Cl_x)_3$ single crystals by heating a solvent (e.g. DMF) may be related to a strong crystal forming affinity between $Br^-$ and $Pb^{2+}$ at elevated temperatures, while $Cl^-$ and $I^-$ may inhibit the formation of mixed halide perovskite single crystals.

In addition to using a proper amount of $CH_3NH_3Cl$, another factor for successful preparation of these single crystals of $CH_3NH_3Pb(Br_{1-x}Cl_x)_3$ mixed halide perovskites may be the total molar amount of $CH_3NH_3^+$ (from the sum of $CH_3NH_3Br$ and $CH_3NH_3Cl$) relative to the amount of $PbBr_2$. In some embodiments of the present invention, the total molar amount of $CH_3NH_3^+$ to the amount of $PbBr_2$ may be set to a ratio of about 1:1. If the $CH_3NH_3Br$:$PbBr_2$ ratio is first fixed to 1:1, it may be unsuccessful at forming $CH_3NH_3Pb(Br_{1-x}Cl_x)_3$ single crystals with additional molar ratios of $CH_3NH_3Cl$. In other cases, it was found that for a molar ratio of $CH_3NH_3Br$ to $PbBr_2$ of greater than about 1.2, $CH_3NH_3PbBr_3$ single crystals were not obtained. Therefore, in some cases excess molar ratios of both $CH_3NH_3Br$ and/or $CH_3NH_3Cl$ may inhibit the crystallization of $CH_3NH_3PbBr_3$. In other cases, crystallization of $CH_3NH_3PbI_3$ may be inhibited by the presence of extra $CH_3NH_3Cl$.

In summary, some embodiments of the present disclosure may include methods for growing mixed halide $CH_3NH_3Pb(Br_{1-x}Cl_x)_3$ single crystals, where the method may include heating a solvent (e.g. DMF) precursor solution containing the reactants. Single and powder crystal diffraction measurements of crystals formed by the methods indicate that Cl may partially replace Br in $CH_3NH_3Pb(Br_{1-x}Cl_x)_3$ perovskite. These $CH_3NH_3Pb(Br_{1-x}Cl_x)_3$ perovskites, with different Cl inclusion amounts, exhibit different electronic structures and the bandgap broadens with increasing Cl inclusion. These growth methods of $CH_3NH_3Pb(Br_{1-x}Cl_x)_3$ perovskite single crystals may provide a facile method for growing $CH_3NH_3Pb(Br_{1-x}Cl_x)_3$ perovskite single crystals which may be used in a number of applications, for example in lasers and photodetectors. These elevated temperature crystallization methods may also be applied to form $CH_3NH_3Pb(Br_{1-x}I_x)_3$, such as $CH_3NH_3PbI_3$, and formamidinium based perovskite $HC(NH_2)_2PbX_3$ (X=I, Br, Cl)

The foregoing discussion and examples have been presented for purposes of illustration and description. The foregoing is not intended to limit the aspects, embodiments, or configurations to the form or forms disclosed herein. In the foregoing Detailed Description of Some Embodiments for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description of Some Embodiments, with each claim standing on its own as a separate aspect, embodiment, or configuration.

What is claimed is:
1. A method comprising:
   contacting a lead halide, a first alkylammonium halide (AAH), and a second AAH in a solvent to form a solution; and maintaining the solution at a first temperature above 21° C., resulting in the formation of an alkylammonium dihalide perovskite crystal, wherein:

the lead halide comprises a first halogen, the first AAH comprises the first halogen, the second AAH comprises a second halogen that is different from the first halogen, the solution has a first molar amount of the first AAH, a second molar amount of the second AAH, and a third molar amount of the lead halide, the first molar amount and the second molar amount are present at a first molar ratio of the first molar amount divided by second molar amount defined by $(1-y)/y$ with $0<y\leq0.5$, the first molar amount, the second molar amount, and the third molar amount are present at a second molar ratio defined by the sum of the first molar amount and the second molar amount divided by the third molar amount where the second molar ratio is between 0.8 and 1.2 inclusively, and the alkylammonium dihalide perovskite crystal comprises lead, the first halogen, and the second halogen.

2. The method of claim 1, wherein the lead halide is selected from the group consisting of $PbBr_2$, $PbI_2$, and $PbCl_2$.

3. The method of claim 1, wherein the first alkylammonium halide comprises at least one of $CH_3NH_3Br$, $CH_3NH_3I$, $CH_3NH_3Cl$, $HC(NH_2)_2I$, $HC(NH_2)_2Br$, or $HC(NH_2)_2Cl$.

4. The method of claim 1, wherein the second alkylammonium halide comprises at least one of $CH_3NH_3Cl$, $CH_3NH_3Br$, $CH_3NH_3I$, $HC(NH_2)_2I$, $HC(NH_2)_2Br$, or $HC(NH_2)_2Cl$.

5. The method of claim 1, wherein the solvent comprises a polar solvent.

6. The method of claim 5, wherein the polar solvent comprises at least one of dimethysulfoxide, dimethylformamide, γ-butyrolactone, or N-methyl-2-pyrrolidone.

7. The method of claim 1, wherein the first temperature is between 40° C. and 100° C.

8. The method of claim 1, wherein the maintaining is for a first period of time between 30 seconds and 100 hours.

9. The method of claim 1, further comprising, prior to the maintaining, heating the solution from a starting temperature to the first temperature.

10. The method of claim 9, wherein the starting temperature is between 0° C. and 30° C.

11. The method of claim 9, wherein the heating is achieved in a second period of time between 1 minute and 10 minutes.

12. The method of claim 1, wherein the lead halide is $PbBr_2$, the first alkylammonium halide is $CH_3NH_3Br$, the second alkylammonium halide is $CH_3NH_3Cl$, the solvent is dimethylformamide, the first temperature is about 50° C., the alkylammonium dihalide perovskite crystal is $CH_3NH_3Pb(Br_{1-x}Cl_x)$, and $0<x\leq0.25$.

* * * * *